United States Patent
Hori et al.

(10) Patent No.: US 6,897,237 B2
(45) Date of Patent: May 24, 2005

(54) MMP-12 INHIBITORS

(75) Inventors: Yozo Hori, Toyonaka (JP); Fumihiko Watanabe, Osaka (JP); Hiroshige Tsuzuki, Kyotanabe (JP); Shingo Furue, Toyonaka (JP); Yoshinori Tamura, Osaka (JP)

(73) Assignee: Shionogi & Co. Ltd., Osaka (JP)

( * ) Notice: Subject to any disclaimer, the term of this patent is extended or adjusted under 35 U.S.C. 154(b) by 151 days.

(21) Appl. No.: 10/257,478

(22) PCT Filed: Apr. 23, 2001

(86) PCT No.: PCT/JP01/03438

§ 371 (c)(1),
(2), (4) Date: Oct. 15, 2002

(87) PCT Pub. No.: WO01/83431

PCT Pub. Date: Nov. 8, 2001

(65) Prior Publication Data

US 2003/0158155 A1 Aug. 21, 2003

(30) Foreign Application Priority Data

Apr. 28, 2000 (JP) ......................................... 2000-130042
Sep. 27, 2000 (JP) ......................................... 2000-293420

(51) Int. Cl.⁷ .................... A61K 31/192; A61K 31/215; C07C 69/612

(52) U.S. Cl. ....................... 514/562; 560/100; 562/400; 562/427; 514/510; 514/557

(58) Field of Search ................................ 514/510, 557, 514/562, 381; 560/100; 562/400, 427, 405, 426; 548/252

(56) References Cited

FOREIGN PATENT DOCUMENTS

| EP | 658559 A1 | 6/1995 |
|---|---|---|
| EP | 757037 A2 | 2/1997 |
| EP | 0 915 086 * | 5/1999 |
| JP | 57-59969 A | 4/1982 |
| JP | 61-236773 A | 10/1986 |
| JP | 63-113455 A | 5/1988 |
| JP | 10-204059 A | 8/1998 |
| JP | 11-35557 A | 2/1999 |
| WO | WO 97 27174 | 7/1997 |
| WO | WO 97/45402 A1 | 12/1997 |
| WO | WO 98/32748 A1 | 7/1998 |
| WO | WO 99/12916 A1 | 3/1999 |
| WO | WO 99 04780 | 4/1999 |
| WO | WO 99/42443 A1 | 8/1999 |
| WO | WO 00/71506 A2 | 5/2000 |
| WO | WO 00/51975 A1 | 9/2000 |
| WO | WO 00/51993 A2 | 9/2000 |
| WO | WO 00/63194 A1 | 10/2000 |

OTHER PUBLICATIONS

Hautamaki et al., "Requirement for Macrophage Elastase for Cigarette Smoke–Induced Emphysema in Mice," Science, 1997, pp. 2002–2004, vol. 277.
Metz et al., "Inhibitors of human neutrophil elastase as a potential treatment for inflammatory diseases," Exp. Opin. Ther. Patents, 1999, pp. 851–895, vol. 9, No. 7, Ashley Publications Ltd.
Ho et al., "Gene expression, purification and characterization of recombinant human neutrophil collagenase," Gene, 1994, pp. 297–301, vol. 146; Elsevier Science.
Okada et al., "Matrix Metalloproteinase 9 (92–kDa Gelatinase/Type IV Collagenase) from HT 1080 Human Fibrosarcoma Cells," Journal of Biological Chemistry, 1992, pp. 21712–21719, vol. 267, No. 30; The American Society for Biochemistry and Molecular Biology, Inc.
Okada et al., "Matrix metalloproteinase 2 from human rheumatoid synovial fibroblasts," Eur. J. Biochem., 1990, pp. 721–730, vol. 194.
Ward et al., "The purification of tissue inhibitor of metalloproteinases–2 from its 72kDa progelatinase complex," Biochem. J., 1991, pp. 179–187, vol. 278.
Knight et al., "A novel coumarin–labelled peptide for sensitive continuous assays of the matrix metalloproteinases," Federation of European Biochemical Societies, 1992, pp. 263–266, vol. 296, No. 3.
Corrie et al., "Synthesis and evaluation of photolabile sulfonamides as potential reagents for rapid photorelease of neuroactive amines," J. Chem. Soc., Perkin Trans. 1. 1996, pp. 1583–1592.

* cited by examiner

Primary Examiner—Golam M M Shameem
(74) Attorney, Agent, or Firm—Foley & Lardner LLP

(57) ABSTRACT

A compound of the formula (I):

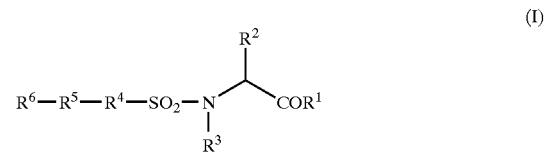

wherein $R^1$ is hydroxy and the like; $R^2$ is optionally substituted lower alkyl and the like; $R^3$ is hydrogen atom and the like; $R^4$ is optionally substituted arylene and the like; $R^5$ is —C≡C— and the like; $R^6$ is optionally substituted naphtyl and the like
its optically active substance, its prodrug, their pharmaceutically acceptable salt, or solvate thereof.

8 Claims, No Drawings

MMP-12 INHIBITORS

TECHNICAL FIELD

This invention relates to sulfonamide derivatives, especially sulfonamide derivatives which selectively inhibit matrix metalloproteinases-12.

BACKGROUND ART

An extracellular matrix, consisting of collagen, fibronectin, laminin, proteoglycan, etc., has a function to support tissues, and plays a role in propagation, differentiation, adhesion, or the like in cells. Metalloproteinases which are protease having a metal ion in the active center, especially matrix metalloproteinases (MMP), are concerned with the degradation of the extracellular matrix. Many types of MMP, from MMP-1 (collagenase type I) to MMP-23, have been reported as enzymes working for the growth, remodeling of tissues, etc. under usual physiological conditions. It is reported, however, that the progression of various kinds of diseases involving breakdown and fibrosis of tissues (e.g., osteoarthritis, rheumatoid arthritis, corneal ulceration, periodontitis, metastasis and invasion of tumor, and virus infection (HIV infection)) is related with increase of the manifestation or activity of the above-mentioned enzyme.

Matrix metalloproteinases-12 (MMP-12) is produced from macrophage and has a character which decomposes elastin and is different from other MMPs'. It is known that this enzyme cleaves collagen type I, collagen type IV, fibronectin, laminin and the like. It is also described in SCIENCE 1997, 277(26), 2002–2004 and Exp. Opin. Ther. Patents(1999) 9(7),851–895 and the like that MMP-12 plays a role in pulmonary emphysema. Therefore, MMP-12 is considered to be involved in the pathogenesis of chronic obstructive pulmonary disease (COPD) which is characterized by respiratory obstruction caused by pulmonary emphysema or chronic bronchitis. It is suggested in Exp. Opin. Ther. Patents (1999) 9(7),851–895 and the like that MMP-12 relates to diseases of metastatic carcinoma, atherosclerosis and the like.

Sulfonamide derivatives having an inhibitory activity against, MMP are described in WO97/27174, WO99/04780 and the like.

No compound having an inhibitory activity against MMP-12 is known.

DISCLOSURE OF INVENTION

The inhibition of such MMP-12 activities is considered to contribute to the improvement and prevention of the above diseases caused by or related to the activity. Therefore, the development of MMP-12 inhibitors has been desired.

In the above situation, the inventors of the present invention have found that certain sulfonamide derivatives having a bisyclic or tricyclic condensed ring at a terminal position have a potent activity to inhibit MMP-12.

The present invention relates to:
1) A compound of the formula (I):

$$R^6-R^5-R^4-SO_2-N(R^3)-CH(R^2)-COR^1 \quad (I)$$

wherein $R^1$ is NHOH, hydroxy, or lower alkyloxy;

$R^2$ is hydrogen atom, optionally substituted lower alkyl, optionally substituted aryl, optionally substituted aralkyl, optionally substituted heteroaryl, or optionally substituted heteroarylalkyl;

$R^3$ is hydrogen atom, optionally substituted lower alkyl, optionally substituted aryl, optionally substituted aralkyl, optionally substituted heteroaryl, or optionally substituted heteroarylalkyl;

$R^4$ is optionally substituted arylene, or optionally substituted heteroarylene;

$R^5$ is a bond, $-(CH_2)_p-$, $-CH=CH-$, $-C\equiv C-$, $-CO-$, $-CO-NH-$, $-N=N-$, $-N(R^A)-$, $-NH-CO-NH-$, $-NH-CO-$, $-O-$, $-S-$, $-SO_2-$, $-SO_2NH-$, $-SO_2-NH-N=CH-$, or a group represented by the formula:

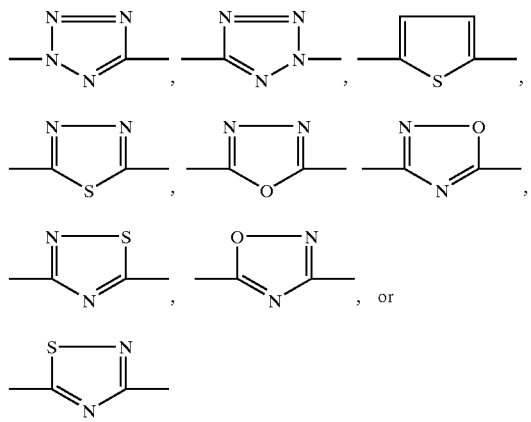

wherein $R^A$ is hydrogen atom or lower alkyl, p is 1 or 2

$R^6$ is optionally substituted naphtyl, optionally substituted isoquinolyl, optionally substituted quinolyl, optionally substituted 1,3-benzodioxolyl, optionally substituted benzofuranyl, or optionally substituted benzothienyl, its optically active substance, its prodrug, their pharmaceutically acceptable salt, or solvate thereof.

In more detail, the invention relates to the following 2)–23).

2) A compound of the formula (II):

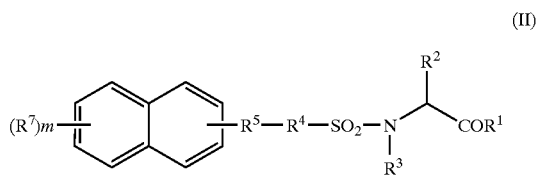

(II)

wherein $R^1$, $R^2$, $R^3$, $R^4$ and $R^5$ are as defined in 1);

$R^7$ is each independently hydrogen atom, halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, aminocarbonyl, acyl, nitro, cyano, or optionally substituted amino;

m is 0, 1, 2, or 3, its optically active substance, its prodrug, their pharmaceutically acceptable salt, or solvate thereof.

3) A compound of the formula (III):

(III)

$(R^7)_m$—[naphthalene]—$R^5$—$R^4$—$SO_2$—N($R^3$)—CH($R^8$)—$COR^1$ wherein $R^1$, $R^3$, $R^4$, and $R^5$ are as defined in 1);
$R^7$ and m are as defined in 2);
$R^8$ is hydrogen atom, lower alkyl optionally substituted with aminocarbonyl or lower alkylthio, aryl optionally substituted with hydroxy, aralkyl optionally substituted with hydroxy, or heteroarylalkyl optionally substituted with hydroxy,
its optically active substance, its prodrug, their pharmaceutically acceptable salt, or solvate thereof.

4) A compound, its optically active substance, its prodrug, their pharmaceutically acceptable salt, or solvate thereof as described in any one of 1) to 3), wherein $R^1$ is hydroxy.

5) A compound, its optically active substance, its prodrug, their pharmaceutically acceptable salt, or solvate thereof as described in any one of 1) to 4), wherein $R^2$ and $R^8$ are hydrogen atom, lower alkyl optionally substituted with aminocarbonyl or lower alkylthio, phenyl optionally substituted with hydroxy, benzyl optionally substituted with hydroxy, or indol-3-ylmethyl optionally substituted with hydroxy.

6) A compound, its optically active substance, its prodrug, their pharmaceutically acceptable salt, or solvate thereof as described in any one of 1) to 5), wherein $R^2$ and $R^8$ are hydrogen atom, methyl, isopropyl, isobutyl, aminocarbonylmethyl, 2-methylthioethyl, 4-hydroxyphenyl, benzyl, 4-hydroxybenzyl, indol-3-ylmethyl, or (5-hydroxy-indol-3-yl)methyl.

7) A compound, its optically active substance, its prodrug, their pharmaceutically acceptable salt, or solvate thereof as described in any one of 1) to 6), wherein $R^3$ is hydrogen atom.

8) A compound, its optically active substance, its prodrug, their pharmaceutically acceptable salt, or solvate thereof as described in any one of 1) to 7), wherein $R^4$ is 1,4-phenylene or 2,5-thiophen-diyl.

9) A compound, its optically active substance, its prodrug, their pharmaceutically acceptable salt, or solvate thereof as described in any one of 1) to 8), wherein $R^5$ is —C≡C—, —CO—NH—, —NH—CO—, —O—, or a group represented by a formula:

[tetrazolyl, triazolyl, oxadiazolyl structures]

10) A compound of the formula (IV):

(IV)

$(R^{12})_m$—[naphthalene]—$R^{11}$—$R^{10}$—$SO_2$—NH—CH($R^9$)—COOH wherein $R^9$ is hydrogen atom, methyl, isopropyl, isobutyl, aminocarbonylmethyl, 2-methylthioethyl, 4-hydroxyphenyl, benzyl, 4-hydroxybenzyl, indol-3-ylmethyl, or (5-hydroxy-indol-3-yl)methyl;
$R^{10}$ is 1,4-phenylene or 2,5-thiophen-diyl;
$R^{11}$ is —C≡C—, —CO—NH—, —NH—CO—, —O—, or a group represented by a formula:

[tetrazolyl, triazolyl, oxadiazolyl structures]

$R^{12}$ is each independently hydrogen atom, halogen, lower alkyl, lower alkyloxy, halo(lower)alkyl, nitro, cyano, optionally substituted amino, or hydroxy;
m is 0, 1, 2, or 3,
its optically active substance, its prodrug, their pharmaceutically acceptable salt, or solvate thereof.

11) A pharmaceutical composition containing a compound of any one of 1) to 10) as an active ingredient.

12) A composition for inhibiting metalloproteinase containing a compound of any one of 1) to 10) as an active ingredient.

13) A composition for inhibiting matrix metalloproteinase containing a compound of any one of 1) to 10) as an active ingredient.

14) A composition for inhibiting matrix metalloproteinase-12 containing a compound of any one of 1) to 10) as an active ingredient.

15) A composition for treating or preventing chronic obstructive pulmonary disease which contains as an active ingredient a compound of any one of 1) to 10).

16) Use of a compound of any one of 1) to 10) for preparation of a pharmaceutical composition for treating chronic obstructive pulmonary disease.

17) A method for treating a mammal, including a human, to alleviate the pathological effects of chronic obstructive pulmonary disease, which comprises administration to said mammal of a compound as described in any one of 1) to 10) in a pharmaceutically effective amount.

18) A method of inhibiting MMP-12, which is characterized by contacting a compound as described in any one of 1) to 10) with MMP-12.

19) A pharmaceutical composition containing as an active ingredient a compound having an inhibitory activity against matrix metalloproteinase-12.

20) A composition for treating or preventing chronic obstructive pulmonary disease containing as an active ingredient a compound having an inhibitory activity against matrix metalloproteinase-12.

21) A method for treating a mammal, including a human, to alleviate the pathological effects of chronic obstructive pulmonary disease, which comprises administration to said mammal of a compound having an inhibitory activity against matrix metalloproteinase-12.

22) Use of a compound having an inhibitory activity against matrix metalloproteinase-12 for preparation of a pharmaceutical composition for treating chronic obstructive pulmonary disease.

23) A method of inhibiting matrix metalloproteinase-12, which is characterized by contacting a compound having an inhibitory activity against matrix metalloproteinase-12 with matrix metalloproteinase-12.

In the present specification, the term "lower alkyl" employed alone or in combination with other terms means a straight- or branched chain monovalent hydrocarbon group having 1 to 8 carbon atom(s). Examples of the alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. C1 to C6 alkyl is preferred. C1 to C3 alkyl is more preferred.

The term "lower alkenyl" employed alone or in combination with other terms in the present specification means a straight- or branched chain monovalent hydrocarbon group having 2 to 8 carbon atoms and at least one double bond. Examples of the alkenyl include vinyl, allyl, propenyl, crotonyl, isopentenyl, a variety of butenyl isomers and the like. C2 to C6 alkenyl is preferred. C2 to C4 alkenyl is more preferred.

The term "lower alkynyl" used in the present specification means a straight- or branched chain monovalent hydrocarbon group having 2 to 8 carbon atoms and at least one triple bond. The alkynyl may contain (a) double bond(s). Examples of the alkynyl include ethynyl, 2-propynyl, 3-butynyl, 4-pentynyl, 5-hexynyl, 6-heptynyl, 7-octynyl and the like. C2 to C6 alkynyl is preferred. C2 to C4 alkynyl is more preferred.

The term "cycloalkyl" used in the present specification includes cycloalkyl group having 3 to 8 carbon atoms. Examples of cycloalkyl group include cyclopropyl, cyclobutyl, cyclopentyl, cyclohexyl, cycloheptyl, cyclooctyl and the like. C3 to C6 cycloalkyl is preferred.

In the present specification, the term "aryl" employed alone or in combination with other terms includes monocyclic or condensed ring aromatic hydrocarbons. Examples include phenyl, 1-naphtyl, 2-naphtyl, anthryl, and the like.

Preferable is phenyl as "aryl" for $R^2$.

Preferable is phenyl as "aryl" for $R^3$.

In the present specification, the term "naphtyl" includes 1-naphtyl and 2-naphtyl.

The term "aralkyl" herein used means the above-mentioned "lower alkyl" substituted with one or more above-mentioned "aryl" at any possible position. Examples of the aralkyl are benzyl, phenylethyl (e.g., 2-phenethyl and the like), phenylpropyl (e.g., 3-phenylpropyl and the like), naphthylmethyl (e.g., 1-naphthylmethyl and 2-naphthylmethyl and the like), anthrylmethyl (e.g., 9-anthrylmethyl and the like), and the like. Benzyl and phenylethyl are preferred.

In the present specification, the term "heteroaryl" employed alone or in combination with other terms includes a 5 to 6 membered aromatic heterocyclic group which contains one or more hetero atoms selected from the group consisting of oxygen, sulfur, and nitrogen atoms in the ring and may be fused with cycloalkyl, aryl, non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazotyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridlinyl (e.g., 2-naphthyridinyl), quinolanyl (2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 3-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl) and the like.

Preferable are indolyl, imidazolyl and the like as "heteroaryl" for $R^2$.

Preferable are pyridyl, thienyl, furyl, imidazolyl and the like as "heteroaryl" for $R^3$.

The term "heteroarylalkyl" herein used includes the above mentioned "lower alkyl" substituted with at least one above-mentioned "heteroaryl" at any possible position. Examples of the heteroarylalkyl are thiazolylmethyl (e.g., 4-thiazolylmethyl), thiazolylethyl (e.g., 5-thiazolyl-2-ethyl), benzothiazolylmethyl (e.g., (benzothiazol-2-yl)methyl), indolylmethyl (e.g., (indol-3-yl)methyl), imidazolylmethyl (e.g., 4-imidazolylmethyl), benzothiazolylmethyl (e.g., 2-benzothiazolylmethyl), indazolylmethyl (e.g., 1-indazolylmethyl), benzotriazolylmethyl (e.g., 1-benzotriazolylmethyl), benzoquinolylmethyl (e.g., 2-benzoquinolylmethyl), benzimidazolylmethyl (e.g., 2-benzimidazolylmethyl), pyridylmethyl (e.g., 4-pyridylmethyl), and the like.

Examples as "heteroarylalkyl" for $R^2$ are indolylmethyl (e.g., indol-3-ylmethyl) and imidazolylmethyl (imidazol-5-ylmethyl) and the like In the present specification, the term "non-aromatic heterocyclic group" includes a 5 to 7 membered non-aromatic ring which contains one or more hetero atoms selected from the group consisting of oxygen, sulfur, and nitrogen atoms in the ring and a condensed ring which are formed with two or more of the non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), 4H-[1,2,4]oxaziazole-5-one, 1,2,3,4-tetrahydro-[1,8]naphtylidine, 1,3-benzodioxolyl and the like.

The term "arylene" herein used means a divalent group of the above-mentioned "aryl". Examples of the arylene are phenylene, naphthylene, and the like. Mentioned in more detail, it is exemplified by 1,2-phenylene, 1,3-phenylen, 1,4-phenylene, and the like. Preferable The term "heteroarylene" herein used means a divalent group of the above-mentioned "heteroaryl". Examples of the heteroarylene are thionphene-diyl, furan-diyl, pyridine-diyl, and the like. Mentioned in more detail, it is exemplified by 2,5-thionphene-diyl, 2,5-furan-diyl, and the like.

In the present specification, the term "acyl" employed alone or in combination with other terms includes alkylcarbonyl in which alkyl group is the above-mentioned "lower alkyl" and arylcarbonyl in which aryl group is the above-mentioned "aryl". Examples of the acyl are acetyl, propionyl, benzoyl, and the like. "Lower alkyl" and "aryl" may be substituted respectively with substituents mentioned below.

The term "halogen" herein used means fluoro, chloro, bromo, and iodo. Fluoro, chloro, and bromo are preferred.

The term "lower alkyloxy" herein used are methyloxy, ethyloxy, n-propyloxy, isopropyloxy, n-butyloxy, isobutyloxy, sec-butyloxy, ter and the like. Methyloxy, ethyloxy, n-propyloxy, isopropyloxy and n-butyloxy are preferred.

The term "lower alkylthio" herein used are methylthio, ethylthio, and the like.

The term "lower alkenyloxy" herein used are vinyloxy, aryloxy, propenyloxy, crotonyloxy, isopentenyloxy and the like.

The term "lower alkyloxycarbonyl" herein used are methyloxycarbonyl, ethyloxycarbonyl, n-propyloxycarbonyl, isopropyloxycarbonyl, and the like.

In the present specification, the term "halo(lower)alkyl" employed alone or in combination with other terms includes the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

Examples of the term "halo(lower)alkyloxy" herein used are trifluoromethyloxy and the like.

Examples of the term "lower alkylsulfonyl" herein used are methylsulfonyl, ethylsulfonyl and the like. Preferable is methylsulfonyl.

Examples of the term "acyloxy" herein used are acetyloxy, propionyloxy, benzoyloxy and the like.

In the present specification, the term "optionally substituted amino" includes amino or amino substituted with one or two of the above mentioned "lower alkyl", "aralkyl", "heteroarylalkyl" or "acyl". Examples of the optionally substituted amino are amino, methylamino, dimethylamino, ethylmethylamino, diethylamino, benzylamino, acetylamino, benzoylamino and the like. Preferable are amino, methylamino, dimethylamino, ethylmethylamino, diethylamino and acetylamino.

Examples of the term "optionally substituted aminocarbonyl" herein used are aminocarbonyl, methylaminocarbonyl, dimethylaminocarbonyl, ethylmethylaminocarbonyl, diethylaminocarbonyl and the like. Preferable is aminocarbonyl, diethylaminocarbonyl.

The substituents of "optionally substituted lower alkyl" are cycloalkyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide and the like. These substituents are able to locate at one or more of any possible positions.

Preferable are hydroxy, lower alkyloxy as substituents of "optionally substituted lower alkyl" for $R^2$.

Preferable are hydroxy, lower alkyloxy, optionally substituted non-aromatic heterocyclic group as substituents of "optionally substituted lower alkyl" for $R^3$.

The substituents of "optionally substituted naphtyl", "optionally substituted isoquinolyl", "optionally substituted quinolyl", "optionally substituted 1,3-benzodioxolyl", "optionally substituted benzofuranyl", "optionally substituted benzothienyl", "optionally substituted arylene", "optionally substituted heteroarylene", "optionally substituted aryl", "optionally substituted heteroaryl", "optionally substituted non-aromatic heterocyclic group", "optionally substituted aralkyl", "optionally substituted heteroarylalkyl", and "optionally substituted ureide" herein used are optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower) alkyloxy, optionally substituted amino, optionally substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide and the like. These substituents are able to locate at one or more of any possible positions.

Preferable are halogen, nitro, cyano, lower alkyloxy, and the like in the above-mentioned substituents as substituents for $R^4$ of "optionally substituted arylene" and "optionally substituted heteroarylene". More preferable are unsubstituted "arylene" and unsubstituted "heteroarylene" as "optionally substituted arylene" and "optionally substituted heteroarylene".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^2$ of "optionally substituted aryl". More preferable are aryl optionally substituted with hydroxy as "optionally substituted aryl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^3$ of "optionally substituted aryl". More preferable are aryl optionally substituted with hydroxy, lower alkyloxy, halogen, or halo (lower)alkyl as "optionally substituted aryl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^2$ of "optionally substituted heteroaryl". More preferable are heteroaryl optionally substituted with hydroxy or halogen as "optionally substituted heteroaryl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^3$ of "optionally substituted heteroaryl". More preferable are heteroaryl optionally substituted with hydroxy, lower alkyloxy, halogen, or halo(lower)alkyl, as "optionally substituted heteroaryl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^2$ of "optionally substituted aralkyl". More preferable are aralkyl optionally substituted with hydroxy as "optionally substituted aralkyl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^3$ of "optionally substituted aralkyl". More preferable are aralkyl optionally substituted with hydroxy, lower alkyloxy, halogen, or halo(lower)alkyl as "optionally substituted aralkyl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^2$ of "optionally substituted heteroarylalkyl". More preferable are heteroarylalkyl optionally substituted with halogen or hydroxy as "optionally substituted heteroarylalkyl".

Preferable are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like in the above-mentioned substituents, as substituents for $R^3$ of "optionally substituted heteroarylalkyl". More preferable are heteroarylalkyl optionally substituted with hydroxy, lower alkyloxy, halogen, or halo(lower)alkyl as "optionally substituted heteroarylalkyl".

Preferable are optionally substituted lower alkyl, cycloalkyl, lower alkenyl, lower alkynyl, hydroxy, lower alkyloxy, lower alkenyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like, as substituents of "optionally substituted naphtyl", "optionally substituted isoquinolyl", "optionally substituted quinolyl", "optionally substituted 1,3-benzodioxolyl", "optionally substituted benzofuranyl", "optionally substituted benzothienyl". More preferable are halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, aminocarbonyl, acyl, nitro, cyano, or optionally substituted amino as substituent. Much more preferable are lower alkyl, lower alkyloxy, halogen, lower alkylthio or optionally substituted amino.

BEST MODE FOR CARRYING OUT THE INVENTION

Compounds (I) of the present invention are able to be synthesized in accordance with the procedure described in WO97/27174 (Method A to F) and WO99/04780.

The term "compound of the present invention" herein used includes a pharmaceutically acceptable salt or its solvate. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like) or by a solvate with an appropriate solvent. These salts and solvates can be formed by the usual method. Preferable are hydrates as a solvates. These hydrates can coordinate with any water molecules.

The present invention includes prodrugs of compounds of the present invention. Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985. For instance, prodrugs such as an ester derivative, optionally substituted alkyloxycarbonyl, which is prepared by reacting a basal acid compound with a suitable alcohol, or an amide derivative, optionally substituted alkylaminocarbonyl, which is prepared by reacting a basal acid compound with a suitable amine are exemplified when the compounds according to present invention have a carboxylic group. Particularly preferred esters as prodrugs are methyl ester, ethyl ester, n-propyl ester, isopropyl ester, n-butyl ester, isobutyl ester, tert-butyl ester, morpholinoethyl ester, and N,N-diethylglycolamido ester, and the like. For instance, prodrugs such as an acyloxy derivative which is prepared by reacting a basal hydroxy compound with a suitable acyl halide or a suitable acid anhydride are exemplified when the compounds according to present invention have a hydroxy group. Particularly preferred acyloxy derivatives as prodrugs —$OCOC_2H_5$, —$OCO(t\text{-}Bu)$, —$OCOC_{15}H_3$, —$OCO(m\text{-}COONa\text{—}Ph)$, —$OCOCH_2CH_2COONa$, —$OCOCH(NH_2)CH_3$, —$OCOCH_2N(CH_3)_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —$NHCO(CH_2)_{20}CH_3$, —$NHCOCH(NH_2)CH_3$, and the like.

The compound of the present invention is not restricted to any particular isomers but includes all possible isomers and racemic modifications.

The compound of the present invention has an excellent activity against inhibiting MMP-12, as described in the following test example.

Definitely, the compounds of the present invention are useful in the treatment of diseases such as chronic obstructive pulmonary disease, osteoarthritis, rheumatoid arthritis, corneal ulceration, periodontal disease, advanced virus infection (e.g., HIV infection), arteriosclerosis obliterans, arteriosclerotic aneurysm, atherosclerosis, restenosis, sepsis, septic shock, coronary thrombosis, aberrant angiogenesis, scleritis, multiple sclerosis, open angle glaucoma, retinopathies, proliferative retinopathy, neovascular glaucoma, pterygium, keratitis, epidermolysis bullosa, psoriasis, diabetes, nephritis, neurodegengerative disease, inflammation, osteoporosis, deossification, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, heart failure, asthmatic respiratory tract disease, arteriosclerosis, and gastric ulcer. The compounds are expected especially as compositions of treating for chronic obstructive pulmonary disease.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 0.1 to 20 mg/kg/day for adult.

The following examples are provided to further illustrate the present invention and are not to be constructed as limiting the scope thereof.

Abbreviations described below are used in the following examples.
Me: methyl
Et: ethyl
n-Pr: n-propyl
i-Pr: isopropyl
n-Bu: n-butyl
i-Bu: isobutyl
t-Bu: tert-butyl
Ph: phenyl
Bn: benzyl
Indol-3-yl methyl: indol-3-ylmethyl
DMSO: dimethyl sulfoxide

EXAMPLE

Example 1

The Preparation of the Compound (A-1)

(Process 1)

To a suspension of L-valine methyl ester hydrochloride (1) (3.30 g, 19.7 mmol), and N-methylmorpholine (5.7 ml, 51.8 mmol) in tetrahydrofuran (100 ml) was added in an ice bath 4-iodobenzenesulfonyl chloride (2) (5.00 g, 16.5 mmol). After the mixture was stirred at 0° C. for 0.5 h and then at room temperature for 2.5 h, the reaction mixture was poured into ice-2mol/L hydrochloric acid and was extracted with ethyl acetate. The organic layer was successively washed with saturated sodium hydrogencarbonate aqueous solution and brine, dried over anhydrous sodium sulfate, and concentrated under reduced pressure. The residue was crystallized from ethyl acetate-hexane to obtain the product (3) (4.32 g, yield: 65.8%) with a melting point of 99–102° C.

IR(KBr, ν max cm$^{-1}$) 3271, 1740, 1568, 1346, 1161
$^1$H NMR (CDCl$_3$,δppm): 0.87 (d, J=6.6 Hz, 3H), 0.96 (d, J=6.8 Hz, 3H), 2.07 (m, 1H), 3.49 (s, 3H), 3.74 (m, 1H), 5.10 (d, J=10.4 Hz, 1H), 7.54 (d, J=8.8 Hz, 2H), 7.86 (d, J=8.4 Hz, 2H)
$[\alpha]_D$+6.7±0.9 (c=0.509, DMSO, 24° C.)
Elemental analysis (C$_{12}$H$_{16}$NO$_4$SI.0.1H$_2$O)
Calcd.: C;36.12, H;4.09, N;3.51, S;8.04, I;31.80
Found: C;36.32, H;4.08, N;3.58, S;7.97, I;31.57

(Process 2)

To a solution of compound (3) (1.00 g, 2.52 mmol) in dimethyl-formamide (6 ml) was added 2-ethynylnaphthalene the mixture was degassed under argon atmosphere. Bis(triphenylphosphine)-palladium (II) dichloride (44.0 mg, 62.7 μmol), copper iodide (I) (24.0 mg, 0.126 μmol) and triethylamine (1.05 ml, 7.56 mmol) were added to it and then the mixture was degassed under argon atmosphere again. After the reaction mixture was stirred at 50° C. for 15 h, it was poured into ice-2mol/L hydrochloric acid and was extracted with ethyl acetate. The organic layer was washed successively with 5% saturated sodium hydrogencarbonate aqueous solution and brine, dried over anhydrous sodium sulfate and evaporated under reduced pressure. The residue was subjected to silica gel column chromatography and the fraction eluted with hexane/ethyl acetate/chloroform=3/1/1 to 2/1/1 was collected, recrystallized from acetone/n-hexane to yield the product (4) (848 mg, yield: 80.0%) with a melting point of 152–154° C.

IR (KBr, ν max cm$^{-1}$) 3288, 2216, 1736, 1597, 1348, 1169
$^1$H NMR (CDCl$_3$, δppm): 0.89 (d, J=6.9 Hz, 3H), 0.98 (d, J=6.6 Hz, 3H), 2.06 (m, 1H), 3.50 (s, 3N), 3.73 (m, 1H), 5.12 (d, J=10.2 Hz, 1H), 7.51–7.60 (m, 3H), 7.67 (d, J=8.7 Hz, 2H), 7.81–7.85 (m, 5H), 8.08 (s, 1H)
$[\alpha]_D$–5.7±0.9 (c=0.504, DMSO, 24° C.)
Elemental analysis (C$_{24}$H$_{23}$NO$_4$S)
Calcd.: C;68.39, H;5.50, N;3.32, S;7.61
Found: C;68.32, H;5.47, N;3.41, S;7.38

(Process 3)

To a solution of compound (4) (818 mg, 1.94 mmol) in dimethylsulfoxide (16.4 ml) was added at room temperature 1 mol/L aqueous sodium hydroxide solution (5.80 ml, 5.82 mmol). The solution was stirred at 60° C. for 15 h and poured into ice-2 mol/L hydrochloric acid. The mixture was extracted with ethyl acetate and the organic layer was washed with brine, dried over anhydrous sodium sulfate and evaporated under reduced pressure. The residue was crystallized from acetone-water to give the product (A-1) (763 mg, yield: 96.5%) with a melting point of 171–173° C.

IR (KBr, v max cm$^{-1}$) 3336, 2214, 1709, 1346, 1167

$^1$H NMR (DMSO-d$_6$, δppm): 0.82 (d, J=6.6 Hz, 3H), 0.84 (d, J=6.6 Hz, 3H), 1.97 (m, 1H), 3.73 (br s, 1H), 7.58–7.67 (m, 3H), 7.76 (d, J=8.4 Hz, 2H), 7.83 (d, J=8.7 Hz, 2H), 7.90–8.01 (m, 3H), 8.15 (d, J=9.0 Hz, 1H), 8.25 (s, 1H), 12.70 (br s, 1H)

[α]$_D$+11.4 ±1.0 (c=0.511, DMSO, 24° C.)

Elemental analysis (C$_{23}$H$_{21}$NO$_4$S.0.3H$_2$O)
Calcd.: C;66.91, H;5.27, N;3.39, S;7.77
Found: C;66.84, H;5.28, N;3.41, S;7.66

The following compound (A-2) to compound (A-30), compound (B-1) to compound (B-29), compound (C-1) to compound (C-2), compound (D-1) to compound (D-2), compound (E-1) to compound (E-10), compound (F-1) to compound (F-2), and compound (G-1) were synthesized in a manner similar to Example 1.

Their results were shown in tables 1 to 5, tables 6 to 9, table 10, table 11, table 12 to 13, table 14, and table 15.

TABLE 1

R$^6$—C≡C—(C$_6$H$_4$)—SO$_2$—NH—*CH(R$^2$)—CO$_2$H

| Example No. | Compound No. | R$^2$ | R$^6$ | * | $^1$H-NMR (DMSO-d$_6$) |
|---|---|---|---|---|---|
| 2 | A-2 | Bn | 2-naphthyl | R | 2.74(dd, J=9.2, 13.6Hz, 1H), 2.98(dd, J=5.2, 13.6Hz, 1H), 3.91(m, 1H), 7.13–7.28(m, 5H), 7.55–7.65(m, 7H), 7.93–8.04(m, 3H), 8.26(s, 1H), 8.44(d, J=9.0Hz, 1H), 12.80(brs, 1H) |
| 3 | A-3 | Bn | 2-naphthyl | S | 2.75(dd, J=9.3, 13.5Hz, 1H), 2.98(dd, J=5.4, 14.1Hz, 1H), 3.93(m, 1H), 7.10–7.23(m, 5H), 7.55–7.67(m, 7H), 7.96–8.01(m, 3H), 8.25(s, 1H), 8.42(d, J=9.0Hz, 1H), 12.00(brs, 1H) |
| 4 | A-4 | (4-OH-indole-3-yl)methyl | 2-naphthyl | R | 2.79(dd, J=8.4, 14.4Hz, 1H), 2.99(dd, J=6.0, 14.4Hz, 1H), 3.95(m, 1H), 6.59(dd, J=2.4, 8.7Hz, 1H), 6.72(d, J=2.4Hz, 1H), 6.98(d, J=2.4Hz, 1H), 7.11(d, J=8.7Hz, 1H), 7.50–7.70(m, 7H), 7.90–8.10(m, 3H), 8.24(s, 1H), 8.34(d, J=8.1Hz, 1H), 8.59(s, 1H), 10.50(s, 1H), 12.65(br s, 1H) |
| 5 | A-5 | i-Pr | 2-naphthyl | R | 0.81(d, J=6.9Hz, 3H), 0.84(d, J=6.9Hz, 3H), 1.97(m, 1H), 3.55(s, 1H), 7.57–7.63(m, 2H), 7.58–7.67(m, 3H), 7.76(d, J=8.4Hz, 2H), 7.83(d, J=9.0Hz, 2H), 7.95–8.01(m, 3H), 8.13(s, 1H), 8.25(s, 1H), 12.4–12.8(brs, 1H) |
| 6 | A-6 | i-Pr | 2-naphthyl | S | 0.81(d, J=6.9Hz, 3H), 0.84(d, J=6.9Hz, 3H), 1.97(m, 1H), 3.48(br, s, 1H), 7.58–7.67(m, 3H), 7.76(d, J=8.4Hz, 2H), 7.83(d, J=8.7Hz, 2H), 7.90–8.01(m, 3H), 8.15(d, J=9.0Hz, 1H), 8.25(s, 6H), 12.60–12.80(brs, 1H) |
| 7 | A-7 | Me | 2-naphthyl | R | 1.19(d, J=7.4Hz, 3H), 3.83(m, 1H), 7.54–7.70(3H), 7.78(d, J=8.2Hz, 2H), 7.85(d, J=8.8Hz, 2H) 7.92–8.06(m, 3H), 8.25(s, 1H), 8.16(brs, 1H), 12.65(brs, 1H) |
| 8 | A-8 | Me | 2-naphthyl | S | 1.19(d, J=7.4Hz, 3H), 3.83(m, 1H), 7.54–7.70(3H), 7.78(d, J=8.2Hz, 2H), 7.85(d, J=8.8Hz, 2H) 7.92–8.06(m, 3H), 8.25(s, 1H), 8.31(brs, 1H), 12.70(brs, 1H) |

TABLE 2

| Example No. | Compound No. | R² | R⁶ | * | ¹H-NMR (DMSO-d₆) |
|---|---|---|---|---|---|
| 9 | A-9 | H | naphthalen-2-yl | | 3.65(d, J=4.8Hz, 2H), 7.66–7.69(3H), 7.78(d, J=8.4Hz, 2H), 7.86(d, J=8.8Hz, 2H), 7.92–8.04(m, 3H), 8.19(m, 1H), 8.25(s, 1H), 12.70(brs, 1H) |
| 10 | A-10 | i-Bu | naphthalen-2-yl | R | 0.74(d, J=6.2Hz, 3H), 0.83(d, J=6.2Hz, 3H), 1.41(t, J=6.6Hz, 2H), 1.60(m, 1H), 3.65(m, 1H), 7.56–7.70(m, 3H), 7.77(d, J=8.4Hz, 2H), 7.83(d, J=8.4Hz, 2H), 7.92–8.04(m, 4H), 8.10(br, 1H), 8.26(s, 1H) |
| 11 | A-11 | i-Bu | naphthalen-2-yl | S | 0.73(d, J=6.6Hz, 3H), 0.83(d, J=6.6Hz, 3H), 1.38–1.45(m, 2H), 1.60(m, 1H), 3.70(m, 1H), 7.56–7.70(m, 3H), 7.77(d, J=8.4Hz, 2H), 7.83(d, J=8.4Hz, 2H), 7.94–8.04(m, 3H), 8.26(s, 1H), 8.30(br s, 1H), 12.70(br, 1H) |
| 12 | A-12 | 4-OH—Ph | naphthalen-2-yl | R | 4.78(s, 1H), 6.64(d, J=8.8Hz, 2H), 7.07(d, J=8.8Hz, 1H), 7.55–7.64(m, 3H), 7.68(d, J=8.8Hz, 2H), 7.77(d, J=8.8Hz, 2H), 7.93–8.04(m, 3H), 8.25(s, 1H), 8.65(br, 1H), 9.45(brs, 1H) |
| 13 | A-13 | 4-OH—Bn | naphthalen-2-yl | R | 2.68(dd, J=7.4, 14.0Hz, 1H), 2.85(dd, J=5.8, 14.0Hz, 1H), 3.72(m, 1H), 6.61(d, J=8.4Hz, 2H), 6.95(d, J=8.4Hz, 2H), 7.55–7.70(m, 7H), 7.92–8.04(m, 3H), 8.25(s, 1H), 9.20(br, 1H) |
| 14 | A-14 | Indole-3-ylmethyl | naphthalen-2-yl | R | 2.89(dd, J=8.0, 14.5Hz, 1H), 3.09(dd, J=5.4, 14.5Hz, 1H), 3.94(m, 1H), 6.90–7.10(m, 3H), 7.27–7.40(m, 2H), 7.52–7.70(m, 7H), 7.92–8.03(m, 3H), 8.25(s, 1H), 8.32(m, 1H), 10.81(s, 1H) |
| 15 | A-15 | Indole-3-ylmethyl | naphthalen-2-yl | S | 2.89(dd, J=8.6, 14.2Hz, 1H), 3.09(dd, J=6.2, 14.2Hz, 1H), 3.95(m, 1H), 6.91–7.14(m, 3H), 7.30–7.38(m, 2H), 7.52–7.67(m, 7H), 7.94–8.06(m, 3H), 8.25(s, 1H), 8.37(m, 1H), 10.82(s, 1H), 12.71(br, 1H) |
| 16 | A-16 | MeS—CH₂—CH₂— | naphthalen-2-yl | R | 1.60–2.00(m, 2H), 1.96(s, 3H), 2.30–2.50(m, 2H), 3.91(s, 1H), 7.50–7.70(m, 3H), 7.78(d, J=8.4Hz, 2H), 7.83(d, J=8.4Hz, 2H), 7.90–8.10(m, 3H), 8.25(s, 1H), 8.33(d, J=8.1Hz, 1H), 12.75(br s, 1H). |

TABLE 3

| Example No. | Compound No. | R² | R⁶ | * | ¹H-NMR (DMSO-d₆) |
|---|---|---|---|---|---|
| 17 | A-17 | MeS—CH₂—CH₂— | naphthalen-2-yl | R | 1.71–1.88(m, 2H), 1.96(s, 3H), 2.25–2.46(m, 2H) 3.91(s, 1H), 7.57–7.68(m, 3H), 7.77(d, J=8.8Hz, 2H), 7.83(d, J=8.8Hz, 2H), 7.96–8.02(m, 3H), 8.26(s, 1H), 8.34(d, J=8.8Hz, 1H), 12.80(brs, 1H) |
| 18 | A-18 | HOOC—CH₂— | naphthalen-2-yl | R | 2.46(dd, J=7.2, 16.5Hz, 1H), 2.63(dd, J=6.6, 16.5Hz, 1H), 4.11(m, 1H), 7.56–7.64(m, 2H), 7.66(dd, J=1.8, 8.4Hz, 1H), 7.77(d, J=8.4Hz, 2H), 7.84(d, J=8.4Hz, 2H), 7.94–8.03(m, 3H), 8.26(s, 1H), 8.38(br s, 1H), 12.67(br s, 2H) |

TABLE 3-continued

| Example No. | Compound No. | R² | R⁶ | * | ¹H-NMR (DMSO-d₆) |
|---|---|---|---|---|---|
| 19 | A-19 | HOOC—CH₂— | naphthalen-2-yl | S | 2.46(dd, J=7.2, 16.5Hz, 1H), 2.63 (dd, J=6.6, 16.5Hz, 1H), 4.11(m, 1H), 7.57–7.64(m, 2H), 7.66(dd, J=1.5, 8.4Hz, 1H), 7.77(d, J=8.7Hz, 2H), 7.84(d, J=8.7Hz, 2H), 7.94–8.03(m, 3H), 8.26(s, 1H), 8.38(br s, 1H), 12.69(br s, 2H) |
| 20 | A-20 | HO—CH₂— | naphthalen-2-yl | R | 3.52(dd, J=6.0, 11.1Hz, 1H), 3.56 (dd, J=5.4, 11.1Hz, 1H), 3.82(dt, J=8.7, 5.4Hz, 1H), 5.10(br s, 1H), 7.56–7.64(m, 2H), 7.65(dd, J=1.5, 8.4Hz, 1H), 7.77(d, J=8.4Hz, 2H), 7.86(d, J=8.4Hz, 2H), 7.94–8.03(m, 3H), 8.20(d, J=9.0Hz, 1H), 8.26(s, 1H), 12.57(br s, 1H) |
| 21 | A-21 | Bn | benzo[1,3]dioxol-5-yl | R | 2.37(dd, J=9.2, 13.8Hz, 1H), 2.96 (dd, J=5.9, 13.4Hz, 1H), 3.90(m, 1H), 5.10(s, 2H), 7.00(d, J=8.8Hz, 1H), 7.05–7.25(7H), 7.56(s, 4H), 8.39(d, J=9.2Hz, 1H), 12.75(br s, 1H) |
| 22 | A-22 | Bn | benzo[1,3]dioxol-5-yl | S | 2.37(dd, J=9.2, 13.8Hz, 1H), 2.96 (dd, J=5.9, 13.4Hz, 1H), 3.90(m, 1H), 5.10(s, 2H), 7.00(d, J=8.8Hz, 1H), 7.05–7.25(7H), 7.56(s, 4H), 8.39(d, J=9.2Hz, 1H), 12.75(br s, 1H) |
| 23 | A-23 | Me | benzo[1,3]dioxol-5-yl | R | 1.17(d, J=7.2Hz, 3H), 3.80(q, J= 8.4Hz, 1H), 6.10(s, 2H), 7.00(dd, J= 1.2, 5.7Hz, 1H), 7.13–7.15(m, 2H), 7.68(d, J=6.9Hz, 2H), 7.79(d, J= 6.9Hz, 2H), 8.26(d, J=8.4Hz, 1H), 12.66(br, 1H) |

TABLE 4

| Example No. | Compound No. | R² | R⁶ | * | ¹H-NMR (DMSO-d₆) |
|---|---|---|---|---|---|
| 24 | A-24 | Me | benzo[1,3]dioxol-5-yl | S | 1.17(d, J=7.2Hz, 3H), 3.80(m, 1H), 6.10(s, 2H), 7.00(d, J=5.7Hz, 1H), 7.13–7.15(m, 2H), 7.68(d, J=6.9Hz, 2H), 7.79(d, J=6.9Hz, 2H), 8.30(m, 1H), 12.60(br, 1H) |
| 25 | A-25 | i-Pr | benzo[1,3]dioxol-5-yl | R | 0.80(d, J=6.3Hz, 3H), 0.83(d, J=6.3Hz, 3H), 1.93(m, 1H), 3.53(m, 1H), 6.10(s, 2H), 7.00(d, J=8.4Hz, 1H), 7.13(d, J=8.4Hz, 1H), 7.15(s, 1H), 7.66(d, J=8.7Hz, 2H), 7.78(d, J=8.7Hz, 2H), 8.11(m, 1H), 12.60(brs, 1H) |
| 26 | A-26 | i-Pr | benzo[1,3]dioxol-5-yl | S | 0.80(d, J=6.6Hz, 3H), 0.83(d, J= 6.6Hz, 3H), 1.93(m, 1H), 3.53(m, 1H), 6.10(s, 2H), 6.99(d, J=7.5Hz, 1H), 7.14(d, J=7.5Hz, 1H), 7.15(s, 1H), 7.66(d, J=8.1Hz, 2H), 7.78(d, J= 8.1Hz, 2H), 8.11(m, 1H), 12.62(br, 1H) |
| 27 | A-27 | H | benzo[1,3]dioxol-5-yl | | 3.62(d, J=4.5Hz, 2H), 6.10(s, 2H), 7.00(m, 1H), 7.12–7.15(m, 2H), 7.67–7.70(m, 2H), 7.80(d, J=8.7Hz, 2H), 8.16(m, 1H), 12.71(brs, 1H) |

TABLE 4-continued

| Example No. | Compound No. | R² | R⁶ | * | ¹H-NMR (DMSO-d₆) |
|---|---|---|---|---|---|
| 28 | A-28 | MeS—CH₂—CH₂— | benzo[1,3]dioxole-5-yl | R | 1.63–1.90(m, 2H), 1.95(s, 1H), 2.26–2.45(m, 2H), 3.87(m, 1H), 6.10(s, 2H), 7.00(d, J=7.8Hz, 2H), 7.12–7.15(m, 2H), 7.68(d, J=8.4Hz, 2H), 7.78(d, J=8.4Hz, 2H), 8.32(d, J=8.7Hz, 1H), 12.78(br, 1H) |
| 29 | A-29 | i-Pr | 2,3-dihydrobenzo[1,4]dioxin-6-yl | R | 0.79(d, J=6.9Hz, 3H), 0.83(d, J=6.9Hz, 3H), 1.94(m, 1H), 3.52(m, 1H), 4.24–4.33(m, 4H), 6.92(d, J=8.1Hz, 1H), 7.04–7.12(m, 2H), 7.66(d, J=8.7Hz, 2H), 7.77(d, J=8.7Hz, 2H), 8.14(d, J=9.3Hz, 1H), 12.66(br s, 1H) |
| 30 | A-30 | i-Pr | 2,3-dihydrobenzo[1,4]dioxin-6-yl | S | 0.79(d, J=6.6Hz, 3H), 0.83(d, J=6.9Hz, 3H), 1.95(m, 1H), 3.53(m, 1H), 4.20–4.40(m, 4H), 6.93(d, J=7.8Hz, 1H), 7.05–7.14(m, 2H), 7.67(d, J=8.1Hz, 2H), 7.78(d, J=8.1Hz, 2H), 8.17(d, J=8.7Hz, 1H), 12.67(br s, 1H) |
| 31 | A-31 | Bn | 2,3-dihydrobenzo[1,4]dioxin-6-yl | R | 2.73(dd, J=9.3, 13.5Hz, 1H), 2.96(dd, J=5.4, 13.5Hz, 1H), 3.90(m, 1H), 6.92(dd, J=0.6, 8.1Hz, 1H), 7.04–7.27(m, 7H), 7.50–7.60(m, 4H), 8.40(d, J=9.3Hz, 1H), 12.77(br s, 1H) |

TABLE 5

| Example No. | Compound No. | R² | R⁶ | * | ¹H-NMR (DMSO-d₆) |
|---|---|---|---|---|---|
| 32 | A-32 | Bn | 6-methoxynaphthalen-2-yl | R | 2.74(dd, J=9.3, 13.5Hz, 1H), 2.97(dd, J=5.4, 13.5Hz, 1H), 3.90(s, 3H), 3.92(m, 1H), 7.13–7.27(m, 6H), 7.39(d, J=2.7Hz, 1H), 7.57–7.64(m, 5H), 7.89(dd, J=4.5, 9.0Hz, 2H), 8.17(s, 1H), 8.45(d, J=8.7Hz, 1H), 12.83(br s, 1H) |
| 33 | A-33 | Bn | 6-methoxynaphthalen-2-yl | S | 2.74(dd, J=9.3, 13.5Hz, 1H), 2.98(dd, J=5.4, 13.5Hz, 1H), 3.91(s, 3H), 3.92(m, 1H), 7.12–7.27(m, 6H), 7.39(d, J=2.4Hz, 1H), 7.57–7.65(m, 5H), 7.89(dd, J=4.5, 8.7Hz, 2H), 8.17(s, 1H), 8.44(d, J=9.0Hz, 1H), 12.81(br s, 1H) |
| 34 | A-34 | i-Pr | 6-methoxynaphthalen-2-yl | R | 0.81(d, J=6.6Hz, 3H), 0.84(d, J=6.9Hz, 3H), 1.96(m, 1H), 3.55(m, 1H), 3.90(s, 3H), 7.24(dd, J=2.7, 9.0Hz, 1H), 7.39(d, J=2.1Hz, 1H), 7.60(dd, J=1.5, 8.7Hz, 1H), 7.73(d, J=8.4Hz, 2H), 7.81(d, J=8.4Hz, 2H), 7.88(dd, J=3.3, 9.0Hz, 2H), 8.16(s, 1H), 8.19(br s, 1H), 12.75(br s, 1H) |
| 35 | A-35 | Me | 6-methoxynaphthalen-2-yl | R | 1.18(d, J=7.2Hz, 3H), 3.82(m, 1H), 3.90(s, 3H), 7.24(dd, J=2.4, 9.0Hz, 1H), 7.39(d, J=2.4Hz, 1H), 7.60(dd, J=1.8, 8.7Hz, 1H), 7.75(d, J=8.4Hz, 2H), 7.82(d, J=8.7Hz, 2H), 7.89(dd, J=3.9, 9.3Hz, 2H), 8.16(s, 1H), 8.29(d, J=7.8Hz, 1H), 12.75(br s, 1H) |

TABLE 6

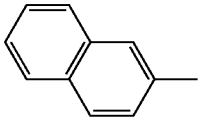

| Example No. | Compound No. | R² | R⁶ | * | ¹H-NMR (DMSO-d₆) |
|---|---|---|---|---|---|
| 31 | B-1 | Bn | 2-naphthyl | R | 2.77(dd, J=9.6, 13.8Hz, 1H), 3.02(d, J=5.1, 13.8Hz, 1H), 3.98(m, 1H), 7.16–7.27(m, 5H), 7.28(d, J=3.9Hz, 1H), 7.33(d, J=3.9Hz, 1H), 7.57–7.66(m, 3H), 7.95–8.03(m, 3H), 8.26(d, J=0.9Hz, 1H), 8.75(d, J=8.1Hz, 1H), 12.91(br s, 1H) |
| 32 | B-2 | Bn | 2-naphthyl | S | 2.76(dd, J=9.4, 13.8Hz, 1H), 3.02(dd, J=4.6, 13.8Hz, 1H), 3.98(m, 1H), 7.15–7.30(m, 5H), 7.28(d, J=3.8Hz, 1H), 7.33(d, J=3.8Hz, 1H), 7.56–7.67(m, 3H), 7.94–8.05(m, 3H), 8.26(s, 1H), 8.79(br s, 1H), 12.96(br, 1H) |
| 33 | B-3 | (Indole-3-yl)methyl | 2-naphthyl | R | 2.95(dd, J=8.1, 14.1Hz, 1H), 3.14(dd, J=5.7, 14.1Hz, 1H), 4.00(dd, J=6.3, 7.2Hz, 1H), 6.97(t, J=7.5Hz, 1H), 7.06(t, J=7.2Hz, 1H), 7.12(d, J=2.4Hz, 1H), 7.23(d, J=3.9Hz, 1H), 7.28(d, J=3.9Hz, 1H), 7.33(d, J=8.1Hz, 2H), 7.43(d, J=7.5Hz, 1H), 7.57–7.67(m, 3H), 7.95–8.03(m, 3H), 8.25(s, 1H), 8.58(br s, 1H), 10.83(s, 1H) |
| 34 | B-4 | i-Pr | 2-naphthyl | R | 0.83(d, J=6.9Hz, 3H), 0.88(d, J=6.6Hz, 3H), 2.01(m, 1H), 3.64(m, 1H), 7.46(d, J=3.9Hz, 1H), 7.54(d, J=3.9Hz, 1H), 7.57–7.66(m, 3H), 7.94–8.02(m, 3H), 8.26(d, J=1.2Hz, 1H), 8.50(d, J=9.0Hz, 1H), 12.77(br s, 1H) |
| 35 | B-5 | i-Pr | 2-naphthyl | S | 0.83(d, J=6.6Hz, 3H), 0.88(d, J=7.0Hz, 3H), 2.02(m, 1H), 3.64(s, 1H), 7.46(d, J=4.0Hz, 1H), 7.54(d, J=4.0Hz, 1H), 7.58–7.66(m, 3H), 7.96–8.02(m, 3H), 8.27(s, 1H), 8.52(brs, 1H), 12.80(brs, 1H) |
| 36 | B-6 | Me | 2-naphthyl | R | 1.25(d, J=7.2Hz, 3H), 3.91(m, 1H), 7.48(d, J=3.9Hz, 1H), 7.55–7.67(m, 4H), 7.95–8.02(m, 3H), 8.26(s, 1H), 8.63(d, J=6.9Hz, 1H), 12.81(br s, 1H) |
| 37 | B-7 | Me | 2-naphthyl | S | 1.24(d, J=7.2Hz, 3H), 3.89(s, 1H), 7.48(d, J=4.0Hz, 1H), 7.56–7.66(m, 4H), 7.96–8.02(m, 3H), 8.27(s, 1H), 8.62(brs, 1H), 12.79(brs, 1H) |

TABLE 7

| Example No. | Compound No. | R² | R⁶ | * | ¹H-NMR (DMSO-d₆) |
|---|---|---|---|---|---|
| 38 | B-8 | 4-OH—Ph | 2-naphthyl | R | 4.87(s, 1H), 6.68(d, J=8.4Hz, 2H), 7.13(d, J=8.7Hz, 2H), 7.39(d, J=3.9Hz, 1H), 7.46(d, J=3.9Hz, 1H), 7.59–7.65(m, 3H), 7.96–8.01(m, 3H), 8.25(s, 1H), 9.01(s, 1H), 9.49(s, 1H), 12.94(br s, 1H) |

TABLE 7-continued

| Example No. | Compound No. | R² | R⁶ | * | ¹H-NMR (DMSO-d₆) |
|---|---|---|---|---|---|
| 39 | B-9 | H | 2-naphthyl | | 3.73(s, 2H), 7.49(d, J=3.9Hz, 1H), 7.57–7.66(m, 4H), 7.95–8.02(m, 3H), 8.26(s, 1H), 8.53(br s, 1H), 12.82(br s, 1H) |
| 40 | B-10 | MeS—CH₂—CH₂— | 2-naphthyl | R | 1.7–2.1(m, 2H), 2.00(s, 3H), 2.3–2.6(m, 2H), 3.97(s, 1H), 7.4–7.7(m, 5H), 7.9–8.1(m, 3H), 8.26(s, 1H), 8.65(br s, 1H), 12.78(br s, 1H). |
| 41 | B-11 | MeS—CH₂—CH₂— | 2-naphthyl | S | 1.76–1.93(m, 2H), 2.00(s, 3H), 2.35–2.50(m, 2H), 3.97(s, 1H), 7.47(d, J=3.8Hz, 1H), 7.54–7.66(m, 4H), 7.96–8.02(m, 3H), 8.26(s, 1H), 8.65(br s, 1H), 12.80(br s, 1H) |
| 42 | B-12 | HOOC—CH₂— | 2-naphthyl | R | 2.4–2.8(m, 2H), 4.19(s, 1H), 7.40–7.70(m, 5H), 7.85–8.06(m, 3H), 8.27(s, 1H), 8.68(br s, 1H), 12.74(br s, 2H). |
| 43 | B-13 | i-Bu | 2-naphthyl | R | 0.79(d, J=6.3Hz, 3H), 0.86(d, J=6.6Hz, 3H), 1.37–1.54(m, 2H), 1.64(m, 1H), 3.78(m, 1H), 7.47(d, J=3.9Hz, 1H), 7.54(d, J=3.9Hz, 1H), 7.57–7.67(m, 3H), 7.94–8.03(m, 3H), 8.26(s, 1H), 8.63(d, J=9.0Hz, 1H), 12.79(br s, 1H) |
| 44 | B-14 | 4-OH—Bn | 2-naphthyl | R | 2.76(dd, J=9.3, 13.5Hz, 1H), 3.01(dd, J=4.8, 13.5Hz, 1H), 3.90(m, 1H), 6.65(d, J=8.4Hz, 2H), 6.97(d, J=8.4Hz, 2H), 7.31(d, J=3.9Hz, 1H), 7.35(d, J=3.9Hz, 1H), 7.56–7.67(m, 3H), 7.94–8.03(m, 3H), 8.26(s, 1H), 8.72(d, J=8.1Hz, 1H), 9.26(s, 1H), 12.86(br s, 1H) |
| 45 | B-15 | HOOC—CH₂—CH₂— | 2-naphthyl | R | 1.71(m, 1H), 1.93(m, 1H), 2.27(t, J=7.5Hz, 2H), 3.89(dd, J=4.8, 8.7Hz, 1H), 7.47(d, J=3.9Hz, 1H), 7.54(d, J=3.9Hz, 1H), 7.58–7.67(m, 3H), 7.94–8.03(m, 3H), 8.27(s, 1H), 8.66(br s, 1H), 12.57(br s, 2H) |

TABLE 8

| Example No. | Compound No. | R² | R⁶ | * | ¹H-NMR (DMSO-d₆) |
|---|---|---|---|---|---|
| 46 | B-16 | Bn | 6-methoxy-2-naphthyl | R | 2.76(dd, J=9.3, 13.5Hz, 1H), 3.01(dd, J=4.8, 13.5Hz, 1H), 3.90(s, 3H), 3.98(m, 1H), 7.16–7.27(m, 6H), 7.27(d, J=3.9Hz, 1H), 7.30(d, J=3.9Hz, 1H), 7.40(d, J=2.4Hz, 1H), 7.59(dd, J=1.8, 8.7Hz, 1H), 7.89(dd, J=5.1, 8.7Hz, 2H), 8.17(s, 1H), 8.77(d, J=8.4Hz, 1H), 12.96(br s, 1H) |
| 47 | B-17 | Bn | 1-naphthyl | R | 2.77(dd, J=9.9, 13.8Hz, 1H), 3.03(dd, J=4.5, 13.5Hz, 1H), 3.89(brs, 1H), 7.15–7.30(m, 5H), 7.32(d, J=3.9Hz, 1H), 7.43(d, J=3.9Hz, 1H), 7.57–7.76(m, 3H), 7.88(d, J=7.2Hz, 1H), 8.05(d, J=7.8Hz, 1H), 8.08(d, J=8.1Hz, 1H), 8.29(d, J=7.8Hz, 1H), 8.78(d, J=7.8Hz, 1H), 12.95(brs, 1H) |

TABLE 8-continued

| Example No. | Compound No. | R² | R⁶ | * | ¹H-NMR (DMSO-d₆) |
|---|---|---|---|---|---|
| 48 | B-18 | Bn | 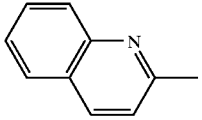 | R | 2.76(dd, J=9.6, 14.0Hz, 1H), 3.03(dd, J=4.6, 14.0Hz, 1H), 4.01(m, 1H), 7.15–7.30(m, 5H), 7.32(d, J=4.0Hz, 1H), 7.47(d, J=4.0Hz, 1H), 7.64–7.90(m, 3H), 8.05(d, J=8.4Hz, 2H), 8.48(d, J=8.4Hz, 2H), 9.80(br s, 1H), 12.85(br, 1H) |
| 49 | B-19 | Bn | 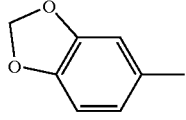 | R | 2.75(dd, J=9.6, 13.8Hz, 1H), 3.00(dd, J=4.8, 13.5Hz, 1H), 3.94(br s, 1H), 6.11(s, 2H), 7.00(d, J=8.1Hz, 1H), 7.12–7.26(m, 9H), 8.71(br s, 1H), 12.89(br s, 1H) |
| 50 | B-20 | Bn | 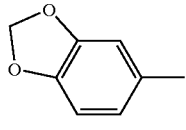 | S | 2.75(dd, J=9.3, 13.2Hz, 1H), 3.00(dd, J=5.1, 13.8Hz, 1H), 3.94(br s, 1H), 6.11(s, 2H), 7.00(d, J=7.7Hz, 1H), 7.12–7.21(m, 9H), 8.71(br s, 1H), 12.89(br s, 1H) |
| 51 | B-21 | H | 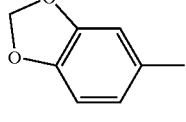 |  | 3.70(s, 2H), 6.11(s, 2H), 7.00(d, J=8.1Hz, 1H), 7.14(m, 1H), 7.16(s, 1H), 7.38(d, J=3.9Hz, 1H), 7.54(d, J=3.9Hz, 1H), 8.47(s, 1H), 12.82(br, 1H) |
| 52 | B-22 | Me | 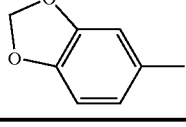 | R | 1.22(d, J=7.2Hz, 3H), 3.88(m, 1H), 6.10(s, 2H), 7.00(d, J=8.1Hz, 1H), 7.14(m, 1H), 7.16(s, 1H), 7.37(d, J=3.9Hz, 1H), 7.52(d, J=3.9Hz, 1H), 8.60(m, 1H), 12.80(br, 1H) |

TABLE 9

| Example No. | Compound No. | R² | R⁶ | * | ¹H-NMR (DMSO-d₆) |
|---|---|---|---|---|---|
| 53 | B-23 | i-Pr | 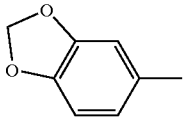 | R | 0.82(d, J=6.6Hz, 3H), 0.86(d, J=6.9Hz, 3H), 2.00(m, 1H), 3.61(dd, J=6.3, 9.3Hz, 1H), 6.11(s, 2H), 7.00(d, J=7.8Hz, 1H), 7.14(m, 1H), 7.16(s, 1H), 7.36(d, J=4.5Hz, 1H), 7.49(d, J=4.5Hz, 1H), 8.47(d, J=9.3Hz, 1H), 12.77(s, 1H) |
| 54 | B-24 | i-Bu | 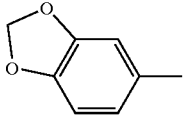 | R | 0.78(d, J=6.6Hz, 3H), 0.85(d, J=6.6Hz, 3H), 1.44–1.45(m, 2H), 1.61(m, 1H), 3.75(brs, 1H), 6.11(s, 2H), 7.00(d, J=8.1Hz, 1H), 7.14(m, 1H), 7.36(d, J=3.9Hz, 1H), 7.49(d, J=3.9Hz, 1H), 8.60(brs, 1H), 12.78(br, 1H) |
| 55 | B-25 | MeS—CH₂—CH₂— | 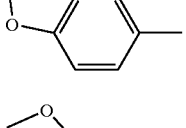 | R | 1.70–1.95(m, 2H), 1.98(s, 3H), 2.33–2.45(m, 2H), 3.94(m, 1H), 6.10(s, 2H), 7.00(d, J=7.8Hz, 1H), 7.12(m, 1H), 7.16(s, 1H), 7.37(d, J=3.9Hz, 1H), 7.50(d, J=3.9Hz, 1H), 8.63(d, J=9.0Hz, 1H), 12.90(brs, 1H) |
| 56 | B-26 | HOOC—CH₂— | 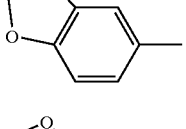 | R | 2.47(dd, J=6.3, 16.2Hz, 1H), 2.68(dd, J=6.3, 16.2Hz, 1H), 4.17(m, 1H), 6.10(s, 2H), 7.00(d, J=8.1Hz, 1H), 7.14(m, 2H), 7.36(d, J=3.9Hz, 1H), 7.51(d, J=3.9Hz, 1H), 8.62(m, 1H), 12.70(br, 2H) |
| 57 | B-27 | Indole-3-yl)methyl | 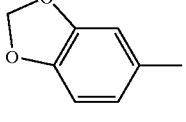 | | |

TABLE 9-continued

| Example No. | Compound No. | R² | R⁶ | * | ¹H-NMR (DMSO-d₆) |
|---|---|---|---|---|---|
| 58 | B-28 | i-Pr | benzodioxane | R | 0.81(s, 3H), 0.86(s, 3H), 1.99(m, 1H), 3.60(m, 1H), 4.24–4.33(m, 4H), 6.92(dd, J=0.3, 8.1Hz, 1H), 7.04–7.12(m, 2H), 7.35(d, J=3.9Hz, 1H), 7.48(d, J=3.9Hz, 1H), 8.47(d, J=9.6Hz, 1H), 12.76(br s, 1H) |
| 59 | B-29 | Bn | benzodioxane | R | 2.74(dd, J=9.6, 13.5Hz, 1H), 3.00(dd, J=4.8, 13.5Hz, 1H), 3.95(m, 1H), 4.20–4.35(m, 4H), 6.93(d, J=8.1Hz, 1H), 7.04–7.30(m, 9H), 8.76(d, J=8.1Hz, 1H), 12.95(br s, 1H) |

TABLE 10

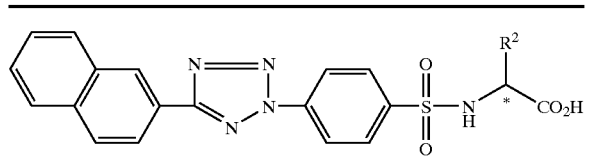

| Example No. | Compound No. | R² | * | ¹H-NMR (DMSO-d₆) |
|---|---|---|---|---|
| 60 | C-1 | Bn | R | 2.76(dd, J=9.6, 13.5Hz, 1H), 3.00(dd, J=4.8, 13.5Hz, 1H), 3.97(brs, 1H), 7.05–7.21(m, 5H), 7.64–7.67(m, 2H), 7.86(d, J=8.7Hz, 2H), 8.06(m, 1H), 8.17–8.31(m, 5H), 8.59(d, J=6.6Hz, 1H), 8.85(s, 1H), 12.95(brs, 1H) |
| 61 | C-2 | Bn | S | 2.76(dd, J=9.3, 13.5Hz, 1H), 3.00(dd, J=5.4, 13.8Hz, 1H), 3.98(brs, 1H), 7.10–7.21(m, 5H), 7.63–7.69(m, 2H), 7.86(d, J=9.0Hz, 2H), 8.06(m, 1H), 8.16–8.31(m, 5H), 8.56(s, 1H), 8.85(s, 1H), 12.92(brs, 1H) |

TABLE 11

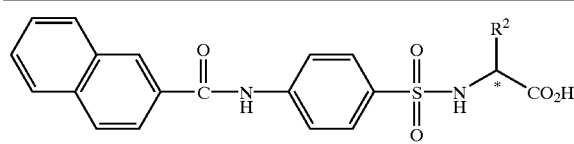

| Example No. | Compound No. | R² | * | ¹H-NMR (DMSO-d₆) |
|---|---|---|---|---|
| 62 | D-1 | Bn | R | 2.74(dd, J=8.6, 13.5Hz, 1H), 2.95(dd, J=5.8, 13.5Hz, 1H), 3.89(m, 1H), 7.10–7.30(m, 5H), 7.58(d, J=8.8Hz, 2H), 7.60–7.72(m, 2H), 7.91(d, J=8.8Hz, 2H), 7.99–8.22(m, 5H), 8.61(s, 1H), 10.73(s, 1H), 12.73(br, 1H) |
| 63 | D-2 | Bn | S | 2.74(dd, J=8.4, 13.5Hz, 1H), 2.95(dd, J=5.8, 13.5Hz, 1H), 3.90(m, 1H), 7.10–7.30(m, 5H), 7.59(d, J=8.8Hz, 2H), 7.60–7.72(m, 2H), 7.91(d, J=8.8Hz, 2H), 8.00–8.20(m, 5H), 8.61(s, 1H), 10.72(s, 1H), 12.73(br, 1H) |

TABLE 12

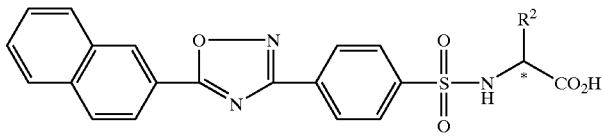

| Example No. | Compound No. | R² | * | ¹H-NMR (DMSO-d₆) |
|---|---|---|---|---|
| 64 | E-1 | Bn | R | 2.76(dd, J=9.3, 13.8Hz, 1H), 2.99(dd, J=5.4, 13.5Hz, 1H), 3.97(m, 1H), 7.13–7.22(m, 5H), 7.66–7.75(m, 2H), 7.79(d, J=8.7Hz, 2H), 8.09(d, J=7.2Hz, 1H), 8.17(d, J=8.1Hz, 2H), 8.22–8.28(m, 3H), 8.54(d, J=9.6Hz, 1H), 8.93(s, 1H), 12.82(br s, 1H) |

TABLE 12-continued

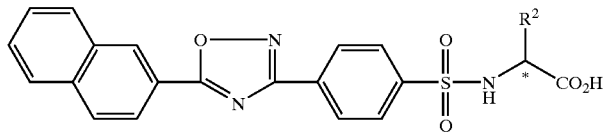

| Example No. | Compound No. | $R^2$ | * | $^1$H-NMR (DMSO-$d_6$) |
|---|---|---|---|---|
| 65 | E-2 | Bn | S | 2.75(dd, J=9.6, 14.0Hz, 1H), 3.00(dd, J=4.8, 13.2Hz, 1H), 3.96(m, 1H), 7.10–7.21(m, 5H), 7.60–7.81(m, 5H), 8.07–8.28(m, 7H), 8.55(d, J=8.8Hz, 1H), 8.93(s, 1H), 12.83(br s, 1H) |
| 66 | E-3 | H | | 3.70(s, 2H), 7.66–7.77(m, 2H), 8.04(d, J=8.7Hz, 2H), 8.09(d, J=7.8Hz, 1H), 8.18–8.36(m, 6H), 8.91(s, 1H), 12.71(br s, 1H) |
| 67 | E-4 | Me | R | 1.21(d, J=6.9Hz, 3H), 3.88(m, 1H), 7.66–7.77(m, 2H), 8.00–8.06(m, 2H), 8.09(d, J=7.8Hz, 1H), 8.18–8.27(m, 3H), 8.29–8.34(m, 2H), 8.39(d, J=7.8Hz, 1H), 8.92(s, 1H), 12.61(br s, 1H) |
| 68 | E-5 | Me | S | 1.21(d, J=6.6Hz, 3H), 3.88(m, 1H), 7.66–7.77(m, 2H), 8.03(d, J=8.7Hz, 2H), 8.08(d, J=7.2Hz, 1H), 8.18–8.27(m, 3H), 8.32(d, J=8.7Hz, 2H), 8.39(d, J=7.5Hz, 1H), 8.91(s, 1H), 12.68(br s, 1H) |
| 69 | E-6 | i-Pr | R | 0.82(d, J=6.6H, 3H), 0.86(d, J=6.9Hz, 3H), 1.99(m, 1H), 3.61(m, 1H), 7.66-7.77(m, 2H), 8.02(d, J=8.7Hz, 2H), 8.09(d, J=7.5Hz, 1H), 8.18–8.33(m, 6H), 8.92(s, 1H), 12.67(br s, 1H) |
| 70 | E-7 | i-Pr | S | 0.82(d, J=6.6H, 3H), 0.86(d, J=6.9Hz, 3H), 1.98(m, 1H), 3.61(t, J=6.9Hz, 1H), 7.66–7.77(m, 2H), 8.00–8.05(m, 2H), 8.09(d, J=7.8Hz, 1H), 8.18–8.33(m, 6H), 8.92(s, 1H), 12.67(br s, 1H) |

TABLE 13

| Example No. | Compound No. | $R^2$ | * | $^1$H-NMR (DMSO-$d_6$) |
|---|---|---|---|---|
| 71 | E-8 | i-Bu | R | 0.75(d, J=6.3Hz, 3H), 0.84(d, J=6.6Hz, 3H), 1.35–1.52(m, 2H), 1.60 (m, 1H), 3.75(m, 1H), 7.66–7.77(m, 2H), 8.02(d, J=8.4Hz, 2H), 8.09(d, J=8.1Hz, 1H), 8.18–8.27(m, 3H), 8.31 (d, J=8.4Hz, 2H), 8.38(d, J=8.4Hz, 1H), 8.92(s, 1H), 12.64(br s, 1H) |
| 72 | E-9 | i-Bu | S | 0.75(d, J=6.3Hz, 3H), 0.84(d, J=6.6Hz, 3H), 1.35–1.52(m, 2H), 1.61 (m, 1H), 3.76(m, 1H), 7.66–7.77(m, 2H), 8.02(d, J=8.4Hz, 2H), 8.09(d, J = 7.2Hz, 1H), 8.18–8.28(m, 3H), 8.31 (d, J=8.4Hz, 2H), 8.38(d, J=7.8Hz, 1H), 8.92(s, 1H), 12.63(br s, 1H) |
| 73 | E-10 | (Indole-3-yl)methyl | R | 2.90(dd, J=8.4, 14.4Hz, 1H), 3.11(d, J=5.7, 14.4Hz, 1H), 4.00(dt, J=8.4, 5.7Hz, 1H), 6.88–7.00(m, 2H), 7.09(d, J=2.4Hz, 1H), 7.21(d, J=7.5Hz, 1H), 7.35(d, J=7.2Hz, 1H), 7.67–7.77(m, 4H), 8.05(d, J=8.7Hz, 2H), 8.09(d, J=7.8Hz, 1H), 8.19–8.29 (m, 3H), 8.47(d, J=8.4Hz, 1H), 8.93 (s, 1H), 10.77(d, J=1.2Hz, 1H), 12.72 (br s, 1H) |

TABLE 14

[Structure: 2-naphthyl-1,2,4-oxadiazole-phenyl-SO2-NH-CH(R2)-CO2H]

| Example No. | Compound No. | R² | * | ¹H-NMR (DMSO-d₆) |
|---|---|---|---|---|
| 74 | F-1 | Bn | R | 2.76(dd, J=9.9, 13.8Hz, 1H), 3.00(d, J=5.1, 13.8Hz, 1H), 3.99(m, 1H), 7.10–7.22(m, 5H), 7.62–7.71(m, 2H), 7.82(d, J=8.4Hz, 2H), 8.05(m, 1H), 8.12–8.22(m, 3H), 8.25(d, J=8.4Hz, 2H), 8.61(d, J=8.4Hz, 1H), 8.77(s, 1H), 12.84(br s, 1H) |
| 75 | F-2 | Bn | S | 2.76(dd, J=9.6, 13.8Hz, 1H), 3.00(d, J=5.1, 13.8Hz, 1H), 3.99(m, 1H), 7.10–7.23(m, 5H), 7.62–7.71(m, 2H), 7.82(d, J=8.4Hz, 2H), 8.05(m, 1H), 8.12–8.22(m, 3H), 8.25(d, J=8.4Hz, 2H), 8.62(d, J=9.3Hz, 1H), 8.77(s, 1H), 12.85(br s, 1H) |

TABLE 15

[Structure: 2-naphthyl-1,3,4-oxadiazole-phenyl-SO2-NH-CH(R2)-CO2H]

| Example No. | Compound No. | R² | * | ¹H-NMR (DMSO-d₆) |
|---|---|---|---|---|
| 76 | G-1 | i-Pr | R | 0.82(d, J=6.9Hz, 3H), 0.86(d, J=6.9Hz, 3H), 1.99(m, 1H), 3.61(m, 1H), 7.69(m, 2H), 8.00–8.10(m, 3H), 8.10–8.40(m, 6H), 8.82(s, 1H), 12.67(br s, 1H) |

Test Example 1 Isolation and Purification of MMP

MMP-1 was purchased from Yagai.

MMP-2 was purchased from Calbiochem-Novabiochem International, Inc.

In regard to MMP-8, catalytic domain ($^{99}$Phe~$^{262}$Gly) was amplified with PCR using commercial available Human Bone Marrow cDNA. This was cloned in *Escherichia. coli* expression vector pTrc99AHE inserted with His-tag sequence and enterokinase digestion-site, induced and expressed by IPTG (Isopropyl-β-D-thiogalactopyranoside) and expressed in a insoluble fraction (Than F. Ho, M. Walid Qoronfleh, Robert C. Wahl, Trica A. Pulvino, Karen J. Vavra, Joe Falvo, Tracey M. Banks, Patricia G. Brake and Richard B. Ciccarelli: Gene expression, purification and characterization of recombinant human neutrophil collagenase. Gene 146, (1994) 297–301, Prepared by the a improved method of this material). Isolation of MMP-8 from insoluble fraction was carried out by dissolving in modifier (6M urea) by a usual method and purification with metal chelate chromatography. And then removing modifier (6M urea) with dialysis and refolding of the enzyme spontaneously gave activated MMP-8.

MMP-9 was isolated and purified by using a combination of procedures described in previous reports as follows. Yasunori Okada, Yukio Gonoji, Katsumi Naka, Katsuro Tomita, Isao Nakanishi, Kazushi Iwata, Kyoko Yamashita, and Taro Hayakawa: Matrix metalloproteinase 9 (92-kDa gelatinase/type IV collagenase) from HT1080 human fibrosarcoma cells. Purification and activation of the precursor and enzymic properties. J. Biol. Chem., 267 (1.992) 21712–21719. Yasunori Okada, Tatsuhisa Morodomi, Jan J, Enghild, Ko Suzuki, Atsushi Yasui, Isao Nakanishi, Guy Salvesen and Hideaki Nagase: Matrix metalloproteinase 2 from human rheumatoid synovial fibroblasts. Purification and activation of the precursor and enzymic properties. Eur. J. Biochem. 194 (1990) 721–730. Robin V Ward, Rosalind M Hembry, John J Reynolds and Gillian Murphy: The purification of tissue inhibitor of metalloproteinase-2 from its 72 kDa progelatinase complex. Biochem. J. 278 (1991) 179–187.

Briefly, human fibrosarcoma ATCC HT1080 cell line was cultured to confluent in Dulbecco's Modified Medium (DMEM) containing 10% fetal-calf serum at 37° C. for 48 hours. Subsequently, the medium of confluent culture was changed to serum-free DMEM medium. To obtain MMP-9, Phorbol-12-myristate-13-acetate (TPA) must be added to this serum-free DMEM medium at a concentration of 50 ng/ml. The TPA treated medium was centrifuged at 3000 rpm for 15 min and the supernatant was concentrated to 450 ml by a Toyo-Roshi UP-20 apparatus with an ultrafiltration membrane. Then, proMMP-9 in this concentrated solution was purified by using columns of Gelatin-Sepharose and Concanavalin A-Sepharose. The pool containing proMMP-9 was dialyzed, concentrated (Toyo-Roshi UP-20) and applied to columns of Sephacryl S-200 and Green A matrix for the separation from TIMPs. The obtained proMMP-9 fraction was activated by TPCK-Trypsin (final conc. 3 μg/μl reaction mix.).

In regard to MMP-12, catalytic domain($^{100}$Phe~$^{263}$Gly) was amplified with RT-PCR from Human Placenta Total RNA. This was cloned in *Escherichia coli* expression vector pTrc99AHE inserted with His-tag sequence and enterokinase digestion-site, induced and expressed by IPTG (Isopropyl-β-D-thiogalactopyranoside) and expressed in a insoluble fraction. Isolation of MMP-12 from a insoluble fraction was carried out by dissolving in modifier (6M urea) by a usual method and purification with metal chelate chromatography (Ni Chelateing Sepharose). And then removing modifier (6M urea) with dialysis and refolding of the enzyme spontaneously gave activated MMP-12.

In regard to MMP-13, mRNA was prepared from carcinoma cell SW1353 derived from human cartilage stimulate by IL-1, TNF and catalytic domain ($^{104}$Tyr~$^{267}$Gly) was amplified with RT-PCR. This was cloned in *Escherichia coli* expression vector pTrc99AHE inserted with His-tag sequence and enterokinase digestion-site, induced and expressed by IPTG (Isopropyl-β-D-thiogalactopyranoside) and expressed in a insoluble fraction. Isolation of MMP-1.3 from a insoluble fraction was carried out by dissolving in modifier (6M urea) by a usual method and purification with metal chelate chromatography (Ni Chelateing Sepharose). And then removing modifier (6M urea) with dialyze and refolding of the enzyme spontaneously gave activated MMP-13.

Test Example 2 Assay for Inhibitory Activities on Various Type of MMPs

The enzymatic activity on MMPs was analyzed by the method described in "C. Graham Knight, Frances Willenbrock and Gillian Murphy: A novel coumarin-labelled peptide for sensitive continuous assays of the matrix metalloproteinases: FEBS LETT., 296, (1992), 263–266". The substrate: MOCAc-Pro-Leu-Gly-Leu-A$_2$Pr(DNP)-Ala-Arg-NH$_2$ was purchased from Peptide Institute, Inc., Osaka, Japan. The measurement of the inhibitory activities (IC$_{50}$) was carried out by the following four methods;

(A) Reaction with substrate, enzyme (MMPs) and inhibitor (B) Reaction with substrate and inhibitor, without enzyme (C) Reaction with substrate and enzyme (MMPs), without inhibitor (D) Reaction with substrate only IC$_{50}$ values were calculated by using the following formula and each fluorescence values of above four methods (A to D).

% inhibition={1−(A−B)/(C−D)}×100

IC$_{50}$ means the concentration required to inhibit 50% of the enzyme activity.

The results are shown in Table 16.

TABLE 16

| Compound No. | MMP-1 (μM) | MMP-2 (μM) | MMP-8 (μM) | MMP-9 (μM) | MMP-12 (μM) | MMP-13 (μM) |
|---|---|---|---|---|---|---|
| A-1 | >10 | 0.40 | 0.57 | 0.77 | 0.0076 | 0.30 |
| A-2 | >10 | >10 | >10 | >10 | 0.016 | >10 |
| A-3 | >10 | >10 | >10 | >10 | 0.021 | >10 |
| A-5 | >10 | 0.11 | 1.06 | 0.33 | 0.014 | 0.34 |
| A-6 | >10 | 0.40 | 0.57 | 0.77 | 0.0076 | 0.30 |
| A-8 | >10 | 0.57 | 2.44 | 3.28 | 0.016 | 2.77 |
| A-9 | >10 | 0.25 | >10 | 1.80 | 0.069 | 2.88 |
| A-10 | >10 | 0.37 | 4.38 | 1.44 | 0.058 | 1.55 |
| A-11 | >10 | 0.37 | 0.58 | 1.27 | 0.0059 | 0.46 |
| A-12 | >10 | 0.37 | 3.63 | 1.79 | 0.035 | 1.14 |
| A-15 | >10 | 0.46 | >10 | 0.90 | 0.032 | 0.89 |
| A-16 | >10 | 0.11 | 1.32 | 0.62 | 0.010 | 0.37 |
| A-17 | >10 | 0.39 | 0.60 | 1.06 | 0.0078 | 0.37 |
| A-22 | >10 | 0.013 | 0.010 | 0.30 | 0.0079 | 0.037 |
| B-1 | >10 | 0.82 | >10 | >10 | 0.042 | >10 |
| B-2 | >10 | >10 | >10 | >10 | 0.24 | >10 |
| B-3 | >10 | 0.18 | 1.40 | 0.75 | 0.016 | >10 |
| B-4 | >10 | 0.24 | 0.54 | 0.53 | 0.011 | 0.64 |
| B-5 | >10 | 2.23 | 2.34 | 3.27 | 0.082 | 6.90 |
| B-6 | >10 | 0.35 | 2.09 | 0.84 | 0.023 | 0.84 |
| B-7 | >10 | 2.03 | 7.79 | 6.31 | 0.16 | >10 |
| B-8 | >10 | 1.12 | 2.65 | 2.11 | 0.048 | 2.30 |
| B-9 | >10 | 1.27 | >10 | 4.23 | 0.26 | 7.18 |
| B-10 | >10 | 0.35 | 1.00 | 0.87 | 0.0088 | 0.95 |
| B-11 | >10 | 1.86 | 2.89 | 4.9 | 0.11 | 6.14 |
| B-12 | >10 | 1.25 | 2.60 | 1.10 | 0.040 | 1.40 |
| B-17 | >10 | >10 | >10 | >10 | 0.82 | >10 |
| C-1 | >10 | 0.14 | >10 | >10 | 0.055 | 0.45 |
| C-2 | >10 | >10 | >10 | >10 | 0.14 | >10 |
| D-2 | >10 | 0.56 | 4.51 | 6.56 | 0.15 | 2.33 |

Test Example 3

Sprague-Dawley male rats (390–430 g initial body weight) were exposed daily to smoke from commercial filtered cigarettes (30 cigarettes/rat/day, 5 days/week, for 7 to 8 weeks) with a smoke-generating and whole-body exposure system. The animals received 30 mg/kg p.o. twice daily of compound (B-6), which was suspended with 0.5% methyl cellulose. Vehicle animals received 2 ml/kg of 0.5% methyl cellulose. At 16-24 hr after the last exposure with cigarette smoke, anesthesia was induced with intraperitoneal injection of 40 mg/kg of pentobarbital sodium. Immediately after muscle relaxation with intravenous pancuronium bromide (0.3 mg/rat), animals were mechanically ventilated with a pressure-limited ventilator and were evaluated dynamic compliance. After exsanguination, the lung was attached to a glass syringe via a connector tube and continuously inflated through the airway to a transpulmonary pressure of 30 $cmH_2O$, deflated them to a Ptp of 0 $cmH_2O$, and aspirated them to a Ptp of −20 $cmH_2O$. The change of Ptp and lung volume was monitored and recorded as the deflation pressure-volume (P-V) curve. Static lung compliance defined as the slope of steep portion of the deflation P-V curve was evaluated. Inspiratory capacity (IC) defined as the difference in lung volume between total lung capacity at a Ptp of 25 $cmH_2O$ and functional residual capacity at a Ptp of 0 $cmH_2O$ was evaluated.

Data are expressed as means ±S.D. Statistical analysis was performed with one-sided Student's t-test. A value of $P<0.05$ was considered significant.

The results were shown in Table 17.

TABLE 17

|  | dynamic compliance (ml/cm$H_2O$/kg) | Static lung compliance (ml/cm$H_2O$/kg) | Inspiratory capacity (ml/kg) | n = |
|---|---|---|---|---|
| Air exposure | 0.84 ± 0.12 | 2.06 ± 0.16 | 21.77 ± 1.63 | 8 |
| Cigarette smoke exposure (Vehicle) | 1.02 ± 0.14 [#] | 2.36 ± 0.38 [#] | 23.74 ± 2.64 [#] | 7 |
| Compound (B-6) Administration | 0.96 ± 0.17 | 2.05 ± 0.25 [*] | 21.76 ± 1.85 | 7 |

[#] P < 0.05 vs. Air exposure
[*] P < 0.05 vs. Cigarette smoke exposure

As shown in Table 17, compound (B-6) significantly reduced the increase of static lung compliance and tended to attenuate the increase of dynamic compliance and inspiratory capacity by cigarette smoke exposure in the rats.

FORMULATION EXAMPLE

Formulation Example 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | |
| --- | --- |
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Industrial Applicability

The sulfonamide derivatives of the present invention have inhibiting activities against the metalloproteinase, especially selectively inhibiting activities agaist MMP-12 and are useful as the treating or preventing agent of chronic obstructive pulmonary disease.

What is claimed is:

1. A compound of the formula (I):

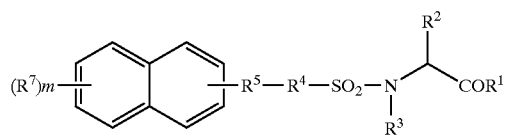

(II)

wherein $R^1$ is NHOH, hydroxy, or lower alkyloxy;

$R^2$ is hydrogen atom, optionally substituted lower alkyl, optionally substituted aryl, or optionally substituted aralkyl;

$R^3$ is hydrogen atom, optionally substituted lower alkyl, optionally substituted aryl, or optionally substituted aralkyl;

$R^4$ is optionally substituted arylene;

$R^5$ is a bond, —(CH$_2$)p—, —CH=CH—, —C≡C—, —CO—, —CO—NH—, —N=N—, —N(R$^A$)—, —NH—CO—NH—, —NH—CO—NH—, —O—, —S—, —SO$_2$—, —SO$_2$NH—, or —SO$_2$—NH—N=CH—, wherein $R^A$ is hydrogen atom or lower alkyl, p is 1 or 2.

$R^7$ is each independently hydrogen atom, halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, aminocarbonyl, acyl, nitro, cyano, or optionally substituted amino;

m is 0, 1, 2, or 3, its optically active substance, its prodrug, their pharmaceutically acceptable salt, or solvate thereof.

2. A compound of the formula (III):

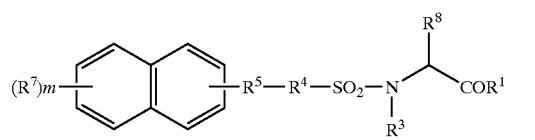

(III)

wherein $R^1$ is NHOH, hydroxy, or lower alkyloxy;

$R^3$ is hydrogen atom, optionally substituted lower alkyl, optionally substituted aryl, or optionally substituted aralkyl;

$R^4$ is optionally substituted arylene;

$R^5$ is a bond, —(CH$_2$)p—, —CH=CH—, —C≡C—, —CO—, —CO—NH—, —N—N—, —N(R$^A$)—, —NH—CO—NH—, —NH—CO—, —O—, —S—, —SO$_2$—, —SO$_2$NH—, or —SO$_2$—NH—N=CH—, wherein $R^A$ is hydrogen atom or lower alkyl, p is 1 or 2;

$R^7$ is each independently hydrogen atom, halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, aminocarbonyl, acyl, nitro, cyano, or optionally substituted amino; and m is 0, 1, 2, or 3;

$R^8$ is hydrogen atom, lower alkyl optionally substituted with aminocarbonyl or lower alkylthio, aryl optionally substituted with hydroxy, aralkyl optionally substituted with hydroxy, its optically active substance, its prodrug, their pharmaceutically acceptable salt, or solvate thereof.

3. A compound of the formula (IV):

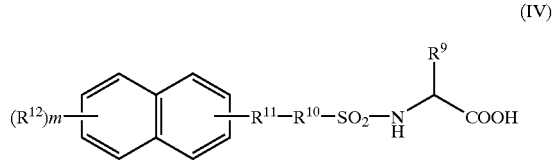

(IV)

wherein $R^9$ is hydrogen atom, methyl, isopropyl, isobutyl, aminocarbonylmethyl, 2-methylthioethyl, 4-hydroxyphenyl, benzyl, or 4-hydroxybenzyl;

$R^{10}$ is 1,4-phenylene;

$R^{11}$ is —C≡C—, CO—NH—, —NHCO—, or —O—;

$R^{12}$ is each independently hydrogen atom, halogen, lower alkyl, lower alkoxy, halo(lower)alkyl, nitro, cyano, optionally substituted amino, or hydroxy;

m is 0, 1, 2, or 3, its optically active substance, its prodrug, their pharmaceutically acceptable salt, or solvate thereof.

4. A pharmaceutical composition comprising a compound of claim 1 as an active ingredient.

5. A method for treating a mammal, including a human, to alleviate the pathological effects of chronic obstructive pulmonary disease, which comprises administration to said mammal of a compound as claimed in claim 1 in a pharmaceutically effective amount.

6. A compound as claimed in claim 1, wherein $R^5$ is a bond, $-(CH_2)_2-$, $-CH=CH-$, $-C\equiv C-$, $-CO-$, $-N=N-$, $-N(R^A)-$, $-NH-CO-NH-$, $-O-$, $-S-$, $-SO_2-$, $-SO_2NH-$, $SO_2-NH-N=CH-$, wherein $R^A$ is hydrogen or lower alkyl;

its optically active substance, its prodrug, their pharmaceutically acceptable salt, or solvate thereof.

7. A compound as claimed in claim 2, wherein $R^5$ is a bond $-(CH_2)_2-$, $-CH=CH-$, $-C\equiv C-$, $-CO-$, $-N=N-$, $-N(R^A)-$, $-NH-CO-NH-$, $-O-$, $-S-$, $-SO_2-$, $-SO_2NH-$, $-SO_2-NH-N=CH-$, where in $R^A$ is a hydrogen or lower alkyl;

its optically active substance, its prodrug, their pharmaceutically acceptable salt, or solvate thereof.

8. A compound as claimed in claim 3, wherein $R^{11}$ is $-C\equiv C-$ or $-O-$;

is optically active substance, its prodrug, their pharmaceutically acceptable salt, or solvate thereof.

* * * * *